US012263000B2

(12) United States Patent
Hung-Cuong Dinh et al.

(10) Patent No.: US 12,263,000 B2
(45) Date of Patent: Apr. 1, 2025

(54) DEVICE FOR DETERMINING THE ELECTRIC POTENTIAL OF THE BRAIN

(71) Applicant: NAOX TECHNOLOGIES, Palaiseau (FR)

(72) Inventors: Hugo Hung-Cuong Dinh, Palaiseau (FR); Khalil Kababe, Beauvais (FR); Emmanuel Lange, Paris (FR)

(73) Assignee: NOAX TECHNOLOGIES, Palaiseau (FR)

( * ) Notice: Subject to any disclaimer, the term of this patent is extended or adjusted under 35 U.S.C. 154(b) by 0 days.

(21) Appl. No.: 18/825,167

(22) Filed: Sep. 5, 2024

(65) Prior Publication Data

US 2024/0423525 A1  Dec. 26, 2024

Related U.S. Application Data

(63) Continuation of application No. 17/640,299, filed as application No. PCT/EP2020/075253 on Sep. 9, 2020, now abandoned.

(30) Foreign Application Priority Data

Sep. 9, 2019  (FR) ...................... 1909895

(51) Int. Cl.
*A61B 5/291* (2021.01)
*A61B 5/00* (2006.01)
(Continued)

(52) U.S. Cl.
CPC ............ *A61B 5/291* (2021.01); *A61B 5/0006* (2013.01); *A61B 5/165* (2013.01); *A61B 5/168* (2013.01);
(Continued)

(58) Field of Classification Search
CPC ..................................... A61B 5/291
See application file for complete search history.

(56) References Cited

U.S. PATENT DOCUMENTS

| 2,798,210 A | 7/1957 | Keitel |
| 2018/0235540 A1 | 8/2018 | Kirszenblat |

(Continued)

OTHER PUBLICATIONS

International Search Report and Written Opinion (with translations) for corresponding PCT application No. PCT/EP2020/075253, mailed Dec. 3, 2020.
(Continued)

*Primary Examiner* — Puya Agahi
(74) *Attorney, Agent, or Firm* — NOTARO, MICHALOS & ZACCARIA P.C.

(57) ABSTRACT

A device for determining a physiological or psychological state of a mammal is disclosed. The device has at least one earpiece with a main body having a body of revolution with an axis of revolution, and an endpiece configured to be inserted into an ear canal. The endpiece has a cylindrical channel intended to receive a body of revolution for detachably mounting the endpiece on the main body, the endpiece being arranged to be movable in rotation about the axis of revolution in order to allow at least one electrode to be oriented toward a zone of the brain of the mammal, and the endpiece having a plurality of electrodes arranged on an outer surface of the endpiece, each electrode being configured to pick up an electrical signal in the ear canal of the mammal.

22 Claims, 6 Drawing Sheets

(51) Int. Cl.
  *A61B 5/16*    (2006.01)
  *A61B 5/268*   (2021.01)
  *A61B 5/27*    (2021.01)
  *A61B 5/305*   (2021.01)
  *A61B 5/31*    (2021.01)
  *A61B 5/372*   (2021.01)

(52) U.S. Cl.
  CPC ............... *A61B 5/268* (2021.01); *A61B 5/27* (2021.01); *A61B 5/305* (2021.01); *A61B 5/31* (2021.01); *A61B 5/372* (2021.01); *A61B 5/4094* (2013.01); *A61B 5/6817* (2013.01); *A61B 5/7203* (2013.01)

(56) References Cited

U.S. PATENT DOCUMENTS

2019/0192077 A1   6/2019   Kaiser
2019/0216619 A1*  7/2019   McDonnall ............... A61F 2/72

OTHER PUBLICATIONS

International Preliminary Report on Patentability Chapter I for corresponding PCT application No. PCT/EP2020/075253, mailed Mar. 17, 2022.

\* cited by examiner

DEVICE FOR DETERMINING THE ELECTRIC POTENTIAL OF THE BRAIN

CROSS-REFERENCES TO RELATED APPLICATIONS

This application is a continuation application of U.S. patent application Ser. No. 17/640,299, filed Mar. 3, 2022; which in turn is a 371 National Stage application of International PCT Application No. PCT/EP2020/075253, filed Sep. 9, 2020; which in turn claims the benefit of priority to French Application No. 1909895 filed Sep. 9, 2020, all of which are herein incorporated by reference in their entirety.

TECHNICAL FIELD

The invention relates to the field of devices for determining a physiological or psychological state of a mammal, in particular devices for determining such a state by measuring an electroencephalogram (EEG) signal.

BACKGROUND

An in-the-ear device for measuring biological data of humans is known, such as the one described in US 2018/0235540. This device comprises an interchangeable part intended to be inserted into an ear canal and provided on its outer surface with electrodes that are intended to detect an electrical signal originating from the heart. This device also comprises a housing on which is mounted an external electrode intended to receive a user's finger in order to form a reference potential.

The replacement of the interchangeable part of these devices is restrictive and complex to carry out. Finally, the detection of electrical signals by the electrodes may lack precision.

SUMMARY

An underlying concept of this invention is to make available a device which serves for measuring biological data and which is easier to operate and is more capable of providing more precise signals.

For this purpose, the invention proposes a device making it possible, for example, to determine a physiological or psychological state of a mammal.

According to one embodiment, the device comprises at least one earpiece comprising:
a main body comprising a cylindrical part having an axis of revolution, and
an endpiece configured to be inserted into an ear canal, said endpiece having a cylindrical channel intended to receive the cylindrical part for detachably mounting the endpiece on the main body, the endpiece being arranged to be movable in rotation about the axis of revolution in order to allow at least one electrode to be oriented toward a zone of the brain of the mammal, and said endpiece comprising a plurality of electrodes arranged on an outer surface of the endpiece, each electrode being configured to pick up an electrical signal in the ear canal of the mammal, and
said device comprising first electrical tracks electrically insulated from each other, arranged in the cylindrical channel of the endpiece and connected to the electrodes, and second electrical tracks electrically insulated from each other, arranged in the cylindrical part of the main body and intended to convey the signal, picked up by the electrodes, to a calculation means.

According to advantageous embodiments, a device of this kind can have one or more of the following features.

According to one embodiment, each of the first electrical tracks, or each of the second electrical tracks, has an annular shape having as its axis said axis of revolution and is arranged in electrical contact with one of said first electrical tracks, or one of said second electrical tracks, independently of the orientation of the endpiece about said axis of revolution, and said first or second electrical tracks of annular shape are spaced along said axis of revolution.

Such a device is advantageous in that it makes it possible to remove the endpiece and replace it with another endpiece in any circumferential orientation, without requiring guide means to ensure the connection between the electrodes and the calculation means. The device is thus less complex to operate. Another advantage of using circular tracks is that they permit rotation of the electrodes about the axis of revolution. The orientation of the endpiece can therefore be easily adjusted, if necessary, such that one or more of the electrodes is oriented toward a specific zone situated around the ear canal. The signals picked up by the electrodes can therefore be more targeted and permit a more precise determination of the physiological or psychological state of the mammal.

The electrodes of the device can be made in many ways. According to one embodiment, at least one electrode has an outer part extending over a longitudinal part, in the direction of the axis of revolution, of the outer surface of the endpiece. According to one embodiment, the electrodes are spaced apart in a circumferential direction about the axis of revolution.

According to one embodiment, at least one electrode has a length equal to or slightly less than the length of the endpiece.

According to one embodiment, at least one electrode has an inner part extending over a part of the cylindrical channel in order to form a first electrical track.

According to one embodiment, the electrodes are spaced apart in a circumferential direction by a constant distance.

According to one embodiment, each of the second electrical tracks is annular, and each of the first electrical tracks is configured to come into contact with a respective second annular electrical track. According to one embodiment, the first electrical tracks extend in an arc of a circle on the inner part of the cylindrical channel about the axis of revolution. According to one embodiment, the first electrical tracks constitute a metallic deposit on the cylindrical channel of the endpiece.

According to another embodiment, each of the first electrical tracks is annular and each of the second electrical tracks forms a contact pad configured to come into contact with a respective first annular electrical track. According to one embodiment, the contact pad extends over an arc of a circle of the cylindrical part of the main body about the axis of revolution. According to an alternative embodiment, the contact pad has a rectangular, semi-spherical, annular or semi-annular shape. According to one embodiment, the contact pad is a metallic deposit on the outer surface of the cylindrical part or of the channel of the endpiece.

The endpieces of the device can be made in different configurations. According to one embodiment, the endpiece is made of elastic material configured to adapt to a dimension, in particular a circumference, of the ear canal so as to ensure contact between the electrodes and the inner surface of the ear canal.

According to one embodiment, the endpiece comprises a polymer material, and at least one electrode comprises a conductive fabric embedded or recessed in the polymer material of the endpiece.

According to an alternative embodiment, the endpiece comprises a polymer material, and at least one electrode comprises a conductive material selected from conductive polymers and silicone doped with nanoparticles, embedded or recessed in the polymer material of the endpiece.

According to another embodiment, the endpiece comprises a polymer material comprising a plurality of conductive parts electrically insulated from one another and forming the electrodes.

According to one embodiment, the device comprises means for locking the endpiece on the cylindrical part of the main body.

According to one embodiment, these locking means comprise a groove and/or a rib and/or a stop arranged in the cylindrical part of the main body and/or in the endpiece.

According to one embodiment, the device comprises a calculation means configured to determine a physiological or psychological state of a mammal as a function of the electrical signals picked up by the electrodes.

According to one embodiment, the device comprises processing means including a measuring device for measuring physical quantities on the electrical signals picked up by the reference electrode and the at least one measuring electrode. These physical quantities are, for example, the intensity or the voltage of the signals picked up by the electrodes.

According to one embodiment, the processing means are configured to amplify the electrical signals picked up by the electrodes before transmission to the measuring device. According to one embodiment, this amplification is achieved by means of an impedance adapter.

According to one embodiment, the plurality of electrodes comprises a reference electrode and at least one measuring electrode.

According to one embodiment, the calculation means is configured to determine the physiological or psychological state as a function of a difference between two electrical signals picked up by two of said electrodes of the earpiece, for example of at least one difference between the electrical signal picked up by one of the measuring electrodes and the electrical signal picked up by the reference electrode. According to one embodiment, any artefacts present on these signals are removed using a multi-channel artefact removal method, for example independent component analysis. According to one embodiment, the difference or differences between the electrical signal picked up by one of the measuring electrodes and the electrical signal picked up by the reference electrode is quantified in the form of a potential difference. According to one embodiment, the calculation means determines this potential difference from the voltage of the signals that is measured by the measuring device.

According to one embodiment, the measuring device makes it possible to measure physical quantities on the electrical signal picked up by the reference electrode by virtue of at least one first resistor in which a current flows that corresponds to a sum between a current corresponding to the electrical signal picked up by the reference electrode and a current coming from a reference generator having known characteristics. According to one embodiment, the at least one resistor can be a single resistor or an electrical assembly made up of several resistors. According to one embodiment, the electrical assembly of several resistors can be an assembly of resistors in series. The physical characteristics of the electrical signal picked up by the reference electrode can be determined by applying Ohm's law to the resistance if it is unique, or by applying a voltage divider bridge formula if one considers an electrical assembly of resistors. In this embodiment, the value of the resistor or resistors used is known.

In one embodiment, the generator is a current generator. In an alternative embodiment, the generator is a voltage generator. The physical characteristics of the electrical signal that is picked up by the reference electrode can be determined by applying Ohm's law to the resistance. In one embodiment, the generator supplying the resistor delivers a voltage current that is considerably high (in absolute value) in relation to the voltage variations expected in the signal picked up by the reference electrode. An advantage of this embodiment is the ability to detect the presence of aberrant values. This embodiment is advantageous in particular for calculating a potential difference between a signal picked up by a measuring electrode and a signal picked up by the reference electrode according to the embodiment below.

According to an advantageous embodiment, the measuring device makes it possible to measure physical quantities on the electrical signal picked up by the at least one measuring electrode by virtue of at least one second resistor in which a current flows that corresponds to a sum between a current corresponding to the electrical signal picked up by the at least one measuring electrode and a current coming from a second generator having known characteristics and delivering a voltage higher than that delivered by the reference generator. According to one embodiment, the at least one resistor can be a single resistor or an electrical assembly made up of several resistors. According to one embodiment, the electrical assembly of several resistors can be an assembly of resistors in series. The physical characteristics of the electrical signal picked up by the reference electrode can be determined by applying Ohm's law to the resistance if it is unique, or by applying a voltage divider bridge formula if one considers an electrical assembly of resistors. According to one embodiment, the voltage delivered by the second generator is positive and of considerably higher value than the voltage variations expected in the signal coming from a measuring electrode.

This advantageous embodiment makes it easy to identify aberrant measurements. Indeed, in this embodiment, it is expected that the potential difference between the voltage of the signal measured by a measuring electrode and the voltage of the signal measured by the reference electrode will fluctuate little around half the sum of the voltage supplying the at least one resistor making it possible to measure the voltage of the signal picked up by the measuring electrode, and the voltage supplying the at least one resistor making it possible to measure the voltage of the signal picked up by the reference electrode. For example, if the resistor (or the assembly of resistors in series) for measuring the voltage of the signal picked up by the measuring electrode is supplied with a voltage of 2.4 V and if the resistor (or the assembly of resistors in series) for measuring the voltage of the signal picked up by the measuring electrode is supplied with a voltage close to 0 V (for example of the order of 0.1 V), and if the voltage fluctuation in the signal picked up by the electrodes is expected around $\mu V$, the potential difference obtained must be around 1.2 V, with fluctuations of the order of $\mu V$. Any measurement that deviates significantly from this value, for example by a few mV, will be considered as an aberrant value.

According to one embodiment, the plurality of electrodes comprises, in addition to the reference electrode and the at least one measuring electrode, a ground electrode. The ground electrode is oriented toward a specific part of the ear canal, said specific part of the ear canal making it possible to pick up a stable signal preferably close to the noise caused by disturbances outside the body of the mammal. According to one embodiment, the endpiece is formed so as to be able to be in contact with the specific part of the ear canal when it is inserted into the ear canal, and the ground electrode is located on a part of the endpiece in contact with the specific part of the ear canal in order to pick up an electrical signal on said specific part of the ear canal. According to one embodiment, the specific part of the ear canal is a mammalian tragus. In the case of a human, the tragus is an ear cartilage located at the entrance to the ear canal.

According to one embodiment, the signal picked up by the ground electrode is used by processing means to effect a noise reduction in the signals measured by the reference electrode and the at least one measuring electrode. According to one embodiment, the noise reduction is achieved by means of a common-mode rejection circuit. This embodiment is advantageous because it makes it possible to reduce the noise originating from disturbances outside the body of the mammal.

According to one embodiment, the ground electrode is connected to a potential corresponding to half the sum of the voltages delivered by two voltage generators, for example the two generators of the measuring device. This embodiment is advantageous because it makes it possible to define identically a zero potential in the whole circuit.

According to one embodiment, the processing means comprise a first resistor connected to a first voltage generator and arranged in such a way as to receive the electrical signal picked up by the reference electrode, and a second resistor connected to a second voltage generator and arranged in such a way as to receive the electrical signal picked up by the at least one measuring electrode, the second voltage generator delivering a voltage greater than that delivered by the first voltage generator.

In the embodiment involving a ground electrode, the reference electrode and the measuring electrodes can be chosen arbitrarily.

According to one embodiment, in particular in the absence of a ground electrode, one of the electrical signals is an electrical reference signal; it is preferably a substantially stable electrical signal. In other words, the reference electrode is defined as the one that picks up a substantially stable electrical signal.

According to one embodiment, the electrical reference signal is measured by an electrode, namely the reference electrode, which is intended to be oriented toward an osseous part near the ear canal of the mammal. In particular, this osseous part is a mastoid.

An advantage of such an arrangement lies in obtaining a stable reference signal, that is to say one that fluctuates little, without requiring the use of an electrode external to the endpiece.

According to one embodiment, the endpiece comprises a marking configured for visually recognizing the reference electrode. According to one embodiment, the reference electrode is connected to a predefined potential.

According to one embodiment, the predefined potential corresponds to half the sum of the voltages delivered by the two aforementioned voltage generators. According to one embodiment, the reference electrode thus connected is placed on the endpiece so as to be in contact with the surface of the ear canal of the mammal. This embodiment is advantageous because it makes it possible to artificially electrify the skin by transmitting to it the potential to which the reference electrode is connected (since the reference electrode is connected to a certain potential and is also affixed to the surface of the ear canal). This makes it possible to increase the stability of the signal picked up by the reference electrode at the surface of the ear canal where it is affixed. Indeed, it is then expected that the signal coming from this part of the ear canal will fluctuate slightly around this potential, while being considerably stable.

According to embodiments, the endpiece comprises means for determining the electrical reference signal. According to one embodiment, the endpiece comprises a marking, preferably on its outer surface, configured to be directed toward the mastoid of the mammal upon insertion of the endpiece into the ear canal of the mammal, so that one of the electrodes is directed toward the mastoid of the mammal. In other words, this marking indicates how to orient one of the electrodes toward an osseous part near the ear canal of the mammal, in particular the mastoid.

According to an alternative embodiment, the reference signal is detected automatically by a selector. In particular, the selector is configured to receive the electrical signals from the electrodes and to detect a reference electrode, said reference electrode being selected as the electrode emitting the electrical signal having the most stable electrical potential, that is to say the one having the fewest fluctuations, among the electrical signals picked up by the electrodes.

According to one embodiment, the signal selector is arranged upstream of the calculation means and connected to the second electrical tracks. According to one embodiment, the selector is connected to an amplifier comprising a negative input and at least one positive input, and the signal selected by the selector is conveyed to the negative input of the amplifier. In particular, the amplifier is connected to the calculation means.

According to one embodiment, the selector is composed of a connection mechanism, for example a reversible connector arranged upstream of the amplifier and of a signal tester arranged downstream of said amplifier. The reversible connector can be adapted to connect each of the second electrical tracks to an input of the amplifier, and the signal tester can be configured to determine a sign of the difference(s) between the signal coming from the at least one positive input and the signal coming from the negative input. The selector can be configured to convey the signals output by the amplifier to the calculation means in response to the signal tester detecting that all the differences are positive. The selector can additionally be configured to modify a configuration of the reversible connector so as to connect another of the second tracks to the negative input of the amplifier in response to the signal tester detecting at least one negative difference among the differences calculated. In this embodiment, the most stable electrical signal is the one having the lowest electrical potential.

According to one embodiment, at least one of the electrodes is oriented toward a temporal lobe of the mammal.

According to one embodiment, the physiological or psychological state relates to an electrical activity of an organ of the mammal, selected from the group consisting of a brain, a heart, a nerve, a muscle and an eye.

According to one embodiment, the physiological or psychological state relates to an EEG signal determined by the calculation means from at least one electrical signal emitted by a zone of the mammal's brain and picked up by one or more of the electrodes arranged in the ear canal.

According to one embodiment, the physiological or psychological state is fatigue of the mammal, a level of attention of the mammal or an epileptic seizure of the mammal.

According to one embodiment, the psychological state is a pre-ictal activity of the brain.

According to one embodiment, the device comprises a means for filtering the electrical signals, said means being configured to attenuate parasitic signals detected by one of said electrodes.

Such parasitic signals may be generated by movements of the mammal and/or of the endpiece in the ear canal and/or may originate from the environment of the device.

According to one embodiment, the filtering means comprises a band-pass filter having a pass band between 0.3 Hz and 50 Hz, in particular between 1 Hz and 40 Hz.

According to one embodiment, the calculation means is configured to:
 determine an electroencephalogram signal of the mammal as a function of the electrical signals measured,
 determine an amplitude of at least one brain wave in a predefined frequency range as a function of said electroencephalogram signal, and
 determine a psychological state as a function of said amplitude of at least one brain wave by comparing said amplitude with a predetermined threshold.

One application of the device is the detection of drowsiness in an individual and the use of this detection to trigger a wake-up for said individual.

According to one embodiment, the main body comprises a wired or wireless data transmission means configured to communicate with the calculation means. The transmission means is configured to transmit the electrical signals, picked up by the electrodes, to the calculation means.

According to one embodiment, the main body is an electrically insulating housing comprising the means for transmitting data to the calculation means and the signal processing means.

According to one embodiment, the device comprises a single earpiece.

According to an alternative embodiment, the device comprises two earpieces. The earpieces are identical or different.

According to a corresponding embodiment, the device comprises two earpieces configured to be arranged respectively in a first ear canal of the mammal and a second ear canal of the mammal and intended to convey respective electrical signals to a calculation means. In particular, the calculation means is intended to determine the physiological or psychological state as a function of a signal measured by an electrode of the earpiece arranged in the first ear canal and a signal measured by an electrode of the earpiece arranged in the second ear canal, in particular as a function of a difference between the two signals.

Thus, in one embodiment, at least one difference between two signals picked up respectively in the ear canal of a left ear and of a right ear of the mammal is exploited.

According to one embodiment, the calculation means is arranged at a distance from the main body.

According to a corresponding embodiment, the device comprises a single calculation means.

According to another embodiment, the calculation means is arranged in the main body of an earpiece.

According to a corresponding embodiment, each earpiece comprises a calculation means.

According to another aspect of the invention, the invention makes available a method for producing a device as described above, in which method at least one electrode is partially or entirely obtained by molding a conductive material, the method comprising a step of molding a polymer in a slide mold in order to form a first solidified component, and a step of molding a liquid or pasty conductive material, preferably conductive polymer or silicone doped with nanoparticles, in said solidified component.

BRIEF DESCRIPTION OF THE FIGURES

The invention will be better understood, and other objects, details, features and advantages thereof will become clearer during the following description of several particular embodiments of the invention, provided solely by way of non-limiting illustration, with reference to the attached drawings.

DETAILED DESCRIPTION

Figure 1:
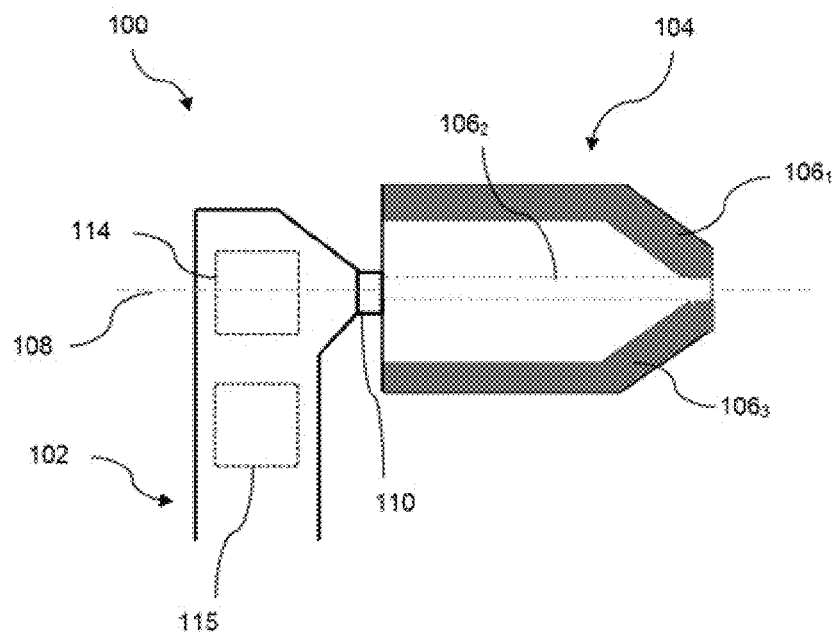
FIG. 1 is a side view of a device according to a first embodiment of the invention.
Figure 2:
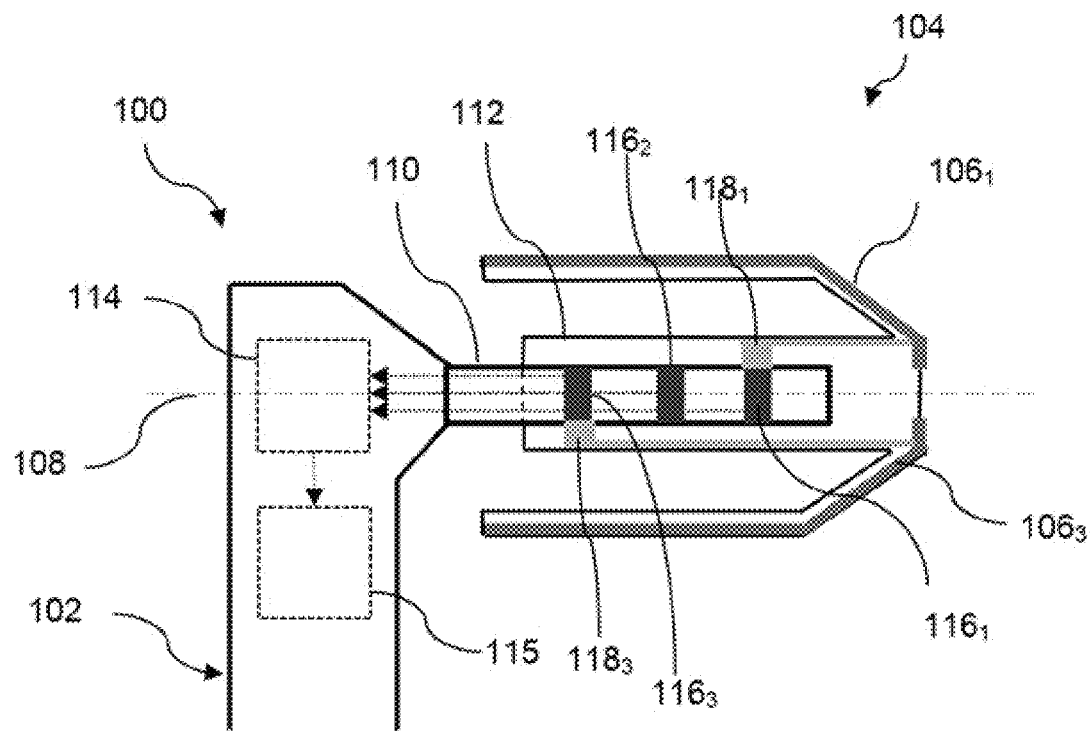
FIG. 2 is a view of the interior of the device in the plane of FIG. 1.

FIGS. 1 and 2 show a first embodiment of a device for determining a psychological or physiological state of a mammal, in particular a person.

The device 100 is provided for determining electroencephalogram (EEG) data of a person. The device 100 comprises an earpiece, for example of a shape and size similar to an earphone, comprising a housing 102 and a detachable endpiece 104.

In FIG. 1, the device is seen from the side, and therefore the parts located outside of the device are visible, while inner or non-visible parts are represented by dotted lines. In FIG. 2, the endpiece 104 is shown in section in the plane of FIG. 1, while the other elements are shown from the side. The elements located inside the housing 102 are represented by dotted lines. The endpiece 104 comprises a convex part and a cylindrical channel 112. The convex part is folded back over a cylindrical channel 112, which is integral with the convex part only in the upper part, as is shown in FIG. 3b. Thus, an empty space is located between the cylindrical channel 112 and the outer surface of the endpiece 104.

The endpiece 104 is provided on its outer surface with three electrodes $106_1$, $106_2$ and $106_3$ configured to pick up electrical signals in an ear canal of the person. The endpiece 104 is a component of revolution about an axis of revolution 108, and the electrodes are arranged equidistant from each other in a circumferential direction of the endpiece 104. The endpiece 104 is made of insulating material, for example silicone, and the electrodes 106 are for example pieces of conductive fabric embedded in the silicone of the endpiece 104, for example by gluing.

The dimensions of the endpiece 104 are configured to adapt to the ear canal. In addition, since the endpiece 104 is made of silicone, the electrodes 106 are kept in contact with an inner wall of the ear canal by virtue of the elasticity of the silicone. The endpiece 104 has a length of between 15 mm and 25 mm and a diameter greater than the diameter of the ear canal, in particular by a percentage of between 2% and 5% of the diameter of the ear canal.

The housing 102 comprises processing means 114 configured to receive the electrical signals picked up by the electrodes 106, process these signals and transform them into digital signals. The processing means 114 are connected to a calculation means 115, which can be integrated in the housing 102 or separate from the latter, in order to determine EEG data as a function of the signals processed by the processing means 114. In another embodiment, the processing means 114 can also be arranged outside the housing 102.

The housing 102 also comprises a shaft 110 extending from the housing 102 and having as its axis the axis of revolution 108. The shaft 110 is configured to receive the cylindrical channel 112 formed in the endpiece 104. The shaft 110 is provided with three annular electrical tracks $116_1$, $116_2$ and $116_3$ respectively connected to the electrodes $106_1$, $106_2$ and $106_3$. The annular tracks 116 have as their axis the axis of revolution 108, and they are arranged at a distance from each other in the direction of the axis of revolution 108. The shaft 110 is made of insulating material, and the electrical tracks 116 are formed by a metal deposit on the shaft 110. The annular tracks 116 are connected to the processing means 114 by electric wires arranged inside the shaft 110. Each of the annular tracks $116_1$ and $116_3$ is connected to an electrode $106_1$ and $106_3$ by first electrical tracks $118_1$ and $118_3$ (the electrical track connecting electrode $106_2$ to annular track $116_2$ is not shown in FIGS. 1 and 2).

Figure 3A:
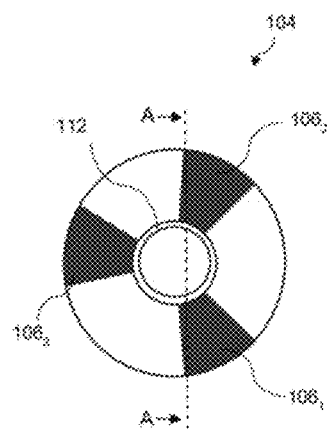
FIGS. 3a and 3b are a plan view and a three-dimensional sectional view, respectively, of the upper part of an endpiece from FIG. 3a that can be used in the device of FIG. 1.
Figure 3B:
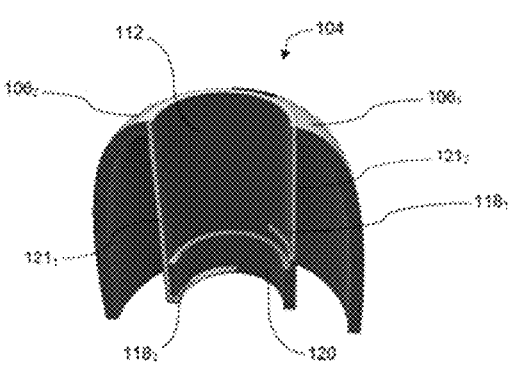

In FIGS. 3a and 3b, the endpiece 104 is shown, respectively, in a top view and in a three-dimensional view along section A-A.

The electrodes 106 extend over the entire length of endpiece 104 in the direction of axis of revolution 108. Moreover, the electrodes 106 are distributed on the outer surface of the endpiece 104 equidistantly about the axis of revolution 108. In particular, the electrodes 106 extend over an outer surface of the endpiece of about 75%, between 50% and 80% of the total outer surface of the endpiece 104. Other distributions of the surface of the electrodes would also be possible.

The first electrical tracks 118 are arranged in the endpiece 104 according to an embodiment shown in FIG. 3b. The upper part of the endpiece 104 has been shown in section there along the axis A of FIG. 3a, so that only two electrodes $106_1$ and $106_2$ and two first electrical tracks $118_1$ and $118_2$ are shown. The endpiece 104 shown in this figure is produced using a slide mold, which makes it possible to obtain three hollow parts on the convex surface of the endpiece 104, said parts being intended to receive the electrodes 106, these hollow parts each extending in the form of an initially empty well inside the insulating part of the endpiece 104. FIG. 3b shows the wells $121_1$ and $121_2$, composed of a vertical portion extending along a longitudinal part of the cylindrical channel 112 and of a horizontal portion extending in an arc of a circle, and intended to receive the electrical tracks $118_1$ and $118_2$. After molding and solidification of the insulating part, a liquid conductive material is poured into each of these wells 121, thus forming the first electrical tracks $118_1$, $118_2$ and $118_3$, each electrical track then occupying a well 121. The liquid conductive material is poured into the wells until they overflow to fill the hollows on the surface of the convex part of the endpiece. The liquid conductive material, having overflowed into the hollows, then solidifies to form the electrodes 106. Since there is no contact between the different hollows and the different wells 121, the respective electrical insulation of the electrodes 106 and of the electrical tracks 118 cast inside is ensured.

Moreover, the cylindrical channel 112 of the endpiece 104 has, on its inner surface, a shoulder 120 shown in FIG. 3b. This serves to hold the endpiece on the shaft 110. In one embodiment, this shoulder 120 may be absent.

In another embodiment, not shown in the figures, the first electrical tracks $118_1$, $118_2$ and $118_3$ are contact pads connected to the electrodes 106 by electrically insulated electrical wires embedded in the surface of the convex part of the endpiece 104 and on the inner surface of the cylindrical channel 112.

In particular, the shaft 110 has a diameter slightly smaller than the diameter of the cylindrical channel 112 of the endpiece 104, for example smaller by a value of between 0.5 mm and 2 mm.

As the first electrical tracks 118 are arranged opposite the annular tracks 116, the endpiece 104 is capable of being rotated about the axis of revolution 108 without risk of interrupting the electrical connection between the electrodes 116 and the processing means 114. Moreover, replacement of the endpiece 104 is thereby facilitated, since there is no need to resort to guide means to provide the electrical connection when mounting the endpiece 104 on the shaft 110.

Figure 4:
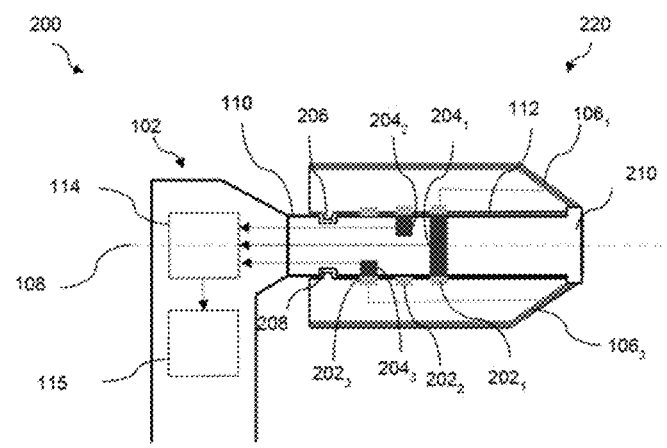
FIG. 4 is a sectional view of a device according to a second embodiment of the invention.

FIG. 4 shows a view similar to FIG. 2 according to a second embodiment. Unlike the device 100, the device 200 of FIG. 4 comprises a solid endpiece 220, with a cylindrical channel 112 hollowed out inside the latter. The solid endpiece 220 further comprises three first annular electrical tracks $202_1$, $202_2$ and $202_3$ arranged in the cylindrical channel 112 and connected to the electrodes $106_1$, $106_2$ and $106_3$, respectively, by electric wires electrically insulated from one another and embedded in the endpiece 220, between its surface and the cylindrical channel 112.

The shaft 110 is provided with three non-annular electrical tracks $204_1$, $204_2$ and $204_3$ spaced apart in the direction of the axis of revolution 108. The non-annular electrical tracks are formed by a metal deposit extending for example according to a semicircle of the shaft around the axis of revolution 108 and projecting in the direction of the solid endpiece 220. The non-annular electrical tracks 204 are arranged facing the annular electrical tracks 202 so as to maintain electrical contact with them.

The shaft 110 has a groove 208 arranged on the side of the housing 102 and configured to receive a collar 206 provided in the cylindrical channel 112 of the endpiece 104. This arrangement makes it possible to block the translation of the solid endpiece 220 in the direction of the axis of revolution 108. The shaft 110 also comprises a stop 210 having a diameter greater than the diameter of the shaft 110, so as to keep the endpiece clamped against the stop 210 in order to stabilize its position in rotation.

Figure 5:
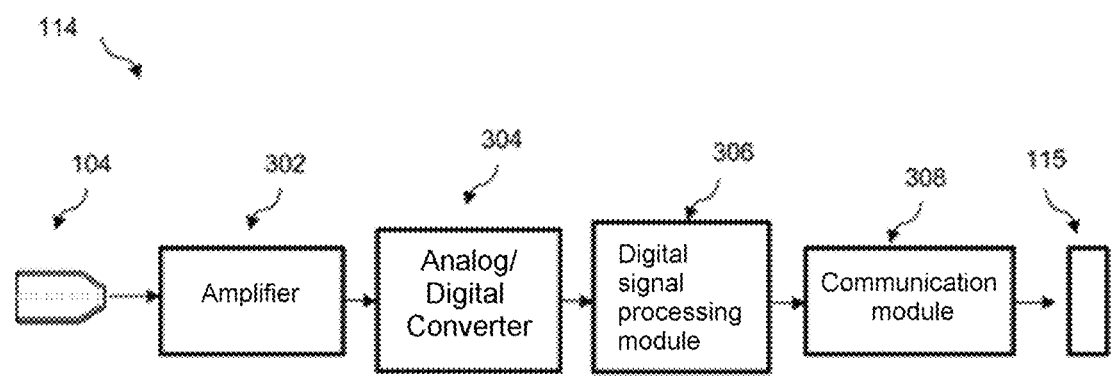
FIG. 5 is a diagram of means for processing an electrical signal, which means can be used in a device according to one embodiment of the invention.

FIG. 5 shows processing means 114 that can be used in the device 100 or 200.

The processing means 114 are configured to receive one or more electrical signals picked up by the electrodes 106. The processing means 114 comprise an amplifier 302 provided to amplify the amplitude of the or each electrical signal. The gain of the amplifier 302 can be between 12 times and 1000 times. In particular, the processing means 114 comprise a preamplifier (not shown in FIG. 5). The amplifier 302 is connected to an analog/digital converter (ADC) 304 configured to digitize the or each electrical signal. The ADC 304 is connected to a digital signal processing module 306 configured to attenuate any parasitic signals picked up by the electrodes. These parasitic signals may be due to the movement of the person's head, to a movement of the electrical wires connected to the device, or to the environment of the device. This digital signal processing module 306 comprises in particular a band-pass filter, but also signal-processing functions, in particular a function for removing the linear component of the signal. This linear component is present on account of choosing a reference electrode inside the ear canal without using a mass located outside the ear canal. The bandwidth of the band-pass filter 306 is further configured to select electrical signals originating from a predetermined organ, particularly the brain. For example, the pass band of the band-pass filter 306 is between 0.3 Hz and 50 Hz, in particular between 1 Hz and 40 Hz. The band-pass filter 306 is connected to a communication module 308 configured to transmit the signals, digitized by the ADC 304 and filtered by the band-pass filter 306, to the calculation means 115, either by wire or wirelessly. The digital signal processing module can also comprise other filters, for example a band-stop filter or notch filter.

The calculation means 115 of the device 100 or 200 is configured to determine an electroencephalogram (EEG) signal as a function of the electrical signals picked up by the electrodes 106, in particular a difference between said electrical signals. The calculation means 115 is configured to determine an EEG signal from one of the combinations of two electrodes among the electrodes: $106_1$, $106_2$ and $106_3$. One of the electrodes is chosen as the reference electrode, against which the potential will be calculated. The brain potential is calculated by taking the difference between the signals picked up by the other electrodes and the signal picked up by the reference electrode. Despite having carried out a first processing of the digital signal in order to eliminate the parasitic signals, for example by having chosen by way of the filter described above a frequency corresponding to the brain waves, artefacts may still be present on the signals. If there are any of these, they are identified by comparing the differences in the signals from the other two electrodes with the reference electrode. Indeed, the two signals then present the same parasitic components. In particular, this comparison is carried out by means of a multi-channel artefact suppression method, preferably independent component analysis.

The choice of the reference electrode is made upstream of the calculation means, according to the following three examples.

In a first example, the reference electrode is identified by means of a marking on the endpiece 104, making it possible to position the latter in the direction of an osseous part of the mammal, for example a mastoid, so as to optimize the stability of the signal, i.e. minimize its fluctuations, in order to obtain a substantially stable signal which can then be used as a reference signal to determine an EEG signal of the mammal.

Figure 8A:
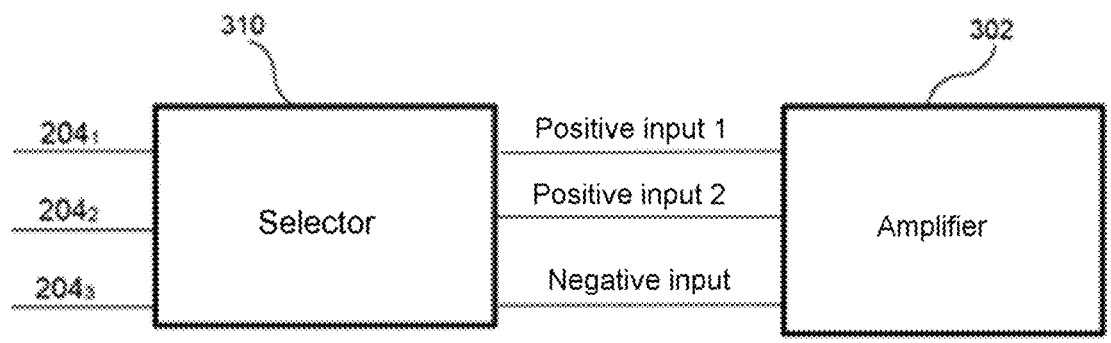
FIGS. 8a and 8b are diagrams of two embodiments of an automatic signal selector.
Figure 8B:
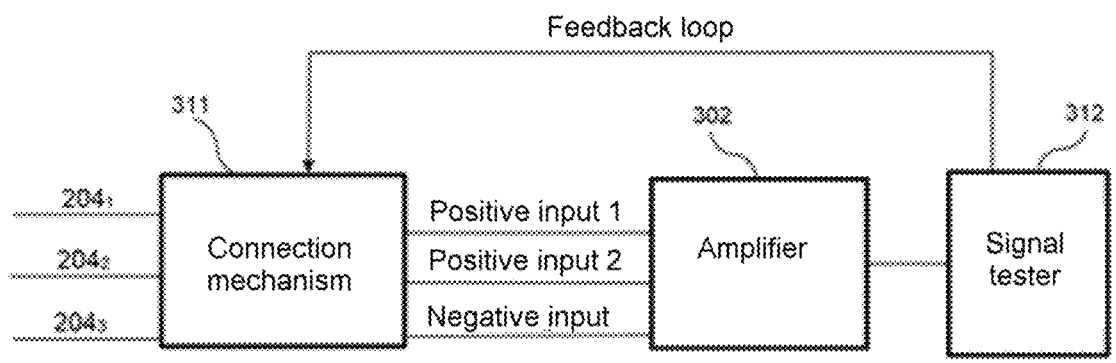

In the other two examples, shown in FIGS. 8a and 8b, an automatic signal selector makes it possible to determine the reference signal.

In a second example, the reference signal is chosen by means of a signal selector 310 placed upstream of the amplifier 302, said selector 310 selecting the most stable signal, that is to say the one that has the fewest fluctuations. The amplifier 302 has one negative input and two positive inputs, the negative input being intended to receive the reference signal. The signal selected as being the most stable is then conveyed to the negative input of the amplifier 302. Thus, the most stable signal is identified and can be used as a reference for calculating the brain potential.

In a third example, the second electrical tracks 118, 204 are connected to the amplifier 302 by way of a connection mechanism 311, which makes it possible to choose the electrical track that is to be connected to each input of the amplifier 302. As in the preceding example, the amplifier 302 has one negative input and two positive inputs. The selector consists of a connection mechanism 311, for example a reversible connector, and a signal tester 312 placed downstream of the amplifier 302. The signal tester 312 is configured to determine the signs of the potential differences between the signals coming from the positive inputs of the amplifier and the signal coming from the negative input, which is then temporarily chosen as reference. The signal chosen for the negative input must be the one with the lowest potential, because it constitutes the potential reference. However, the lowest potential is assumed to coincide with the most stable signal. If the signal tester 312 determines that the potential differences between the signals coming from the positive inputs of the amplifier and the signal coming from the negative input are all positive, the signal chosen for the negative input is indeed the most stable, and the signals at the output of the amplifier can then be conveyed to the calculating means 115 (first passing through the rest of the processing means 114). The signal coming from the negative input of the amplifier will be chosen as the potential reference. Otherwise, if at least one of the differences is negative, this means that the signal chosen for the negative input was not the one with the lowest potential. In this case, a feedback loop sends a signal to the connection mechanism 311, which modifies the input connections of the amplifier 302, and then the test is performed again by the signal tester. The connections are thus modified and the test carried out until the correct configuration is found, that is to say the configuration in which the calculated differences are all positive.

For example, if the electrode chosen as a reference, manually, according to the first example set out above, or automatically, according to either of the second and third examples set out below, is the electrode $106_3$, the EEG signal can thus be obtained from signals detected by the electrodes $106_1$ and $106_3$ or the electrodes $106_2$ and $106_3$.

The earpiece described above can be used alone or in combination with a second earpiece.

Figure 6:
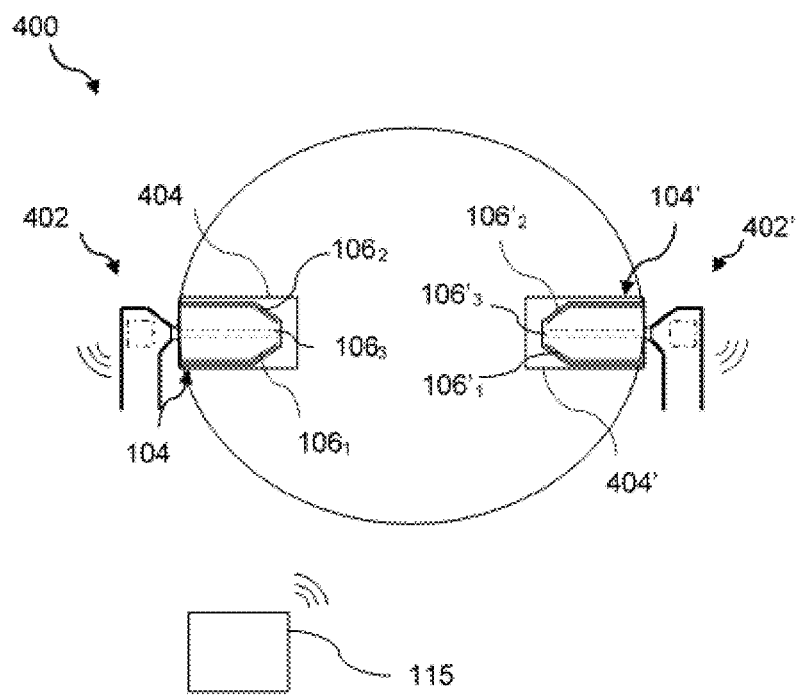
FIG. 6 is a diagram of a device according to a third embodiment of the invention.

Thus, the device 400 of FIG. 6 comprises two earpieces 402 and 402', similar to the earpiece of the device 100 or 200. Each earpiece 402 and 402' is provided with an endpiece 104 and 104' similar to the endpiece of the device 100 or 200. Each endpiece 104 and 104' is arranged in an ear canal 404 and 404' of the person wearing the device 400. Unlike the devices 100 and 200, the calculation means 115 is arranged at a distance from the earpieces 402, and the processing means 114 transmit the electrical signals, received by the electrodes 106, wirelessly to the calculation means 115. The calculation means 115 can also be incorporated in one of the two earpieces.

The endpieces 104 are made of elastic material and dimensioned to ensure contact between the wall of the ear canals and the electrodes 106 and 106' of the endpieces 104 and 104', respectively.

The calculation means 115 is configured to determine an electroencephalogram (EEG) signal as a function of the electrical signals picked up by a combination of two electrodes chosen from the following combinations: $106_1$ and $106'_3$, $106_2$ and $106'$, $106_3$ and $106'3$, $106'_1$ and $106'_3$, $106'_2$ and $106'_3$. In particular, the EEG signal is determined by a difference between the two signals in combination. As in the case of operation with one earpiece, artefacts still present in the signal are removed by means of a multi-channel artefact removal method, preferably by independent component analysis.

In this embodiment with two earpieces, the reference electrode is chosen according to one of the examples presented in the mode of operation with one earpiece. For example, if the chosen reference electrodes are $106_3$ and $106'_3$, the EEG signal can thus be obtained from signals detected by one of the following combinations of electrodes: $106_1$ and $106_3$, $106_2$ and $106_3$, $106'_1$ and $106'_3$, $106'_2$ and $106'_3$, $106_1$ and $106'_3$, $106_2$ and $106'_3$, $106'_1$ and $106_3$, and $106'_2$ and $106_3$.

Figure 7:
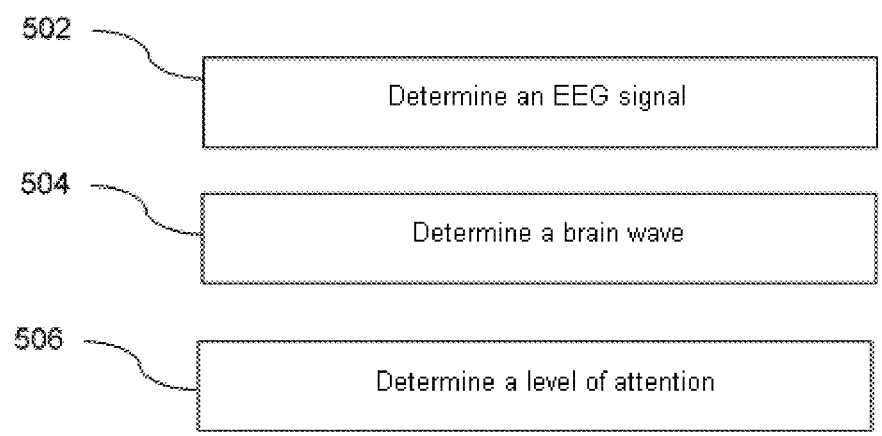
FIG. 7 is a diagram of a data processing method that can be implemented by a calculation means of the device according to one embodiment of the invention.

FIG. 7 shows the steps performed by the calculation means 115 of the device 100, 200 or 400 in order to determine a level of attention of the person wearing the device 100, 200 or 400.

The calculation means 115 is configured to perform:
a step 502 for determining an EEG signal as a function of the difference between two signals picked up by two electrodes of the same earpiece or of two earpieces,
a step 504 for determining a brain wave as a function of the frequency of the EEG signal. By way of example, if the frequency of the signal is between 5 Hz and 15 Hz, in particular equal to 10 Hz, the brain wave is of the α type, and, if the frequency of the signal is between 15 Hz and 25 Hz, in particular equal to 20 Hz, the brain wave is of the β type. The brain wave can be determined by any signal processing means, in particular by applying a Fourier transform,
a step 506 for determining a level of attention as a function of the brain wave. In particular, the level of attention is determined as a function of the amplitude of the brain wave or of the ratio between two amplitudes of two brain waves. By way of example, for a brain wave of the α type, the calculation means 115 determines that the person lacks attention for an amplitude of the α wave below a first predetermined threshold. For a brain wave of the β type, the calculation means 115 determines that the person lacks attention for an amplitude of the β wave below a second predetermined threshold. In particular, the calculation means 115 determines the level of attention by comparing the ratio of amplitudes of the α and β waves to a third predetermined threshold.

In one embodiment, the calculation means 115 can comprise a step of triggering a wake-up signal intended to wake the person wearing the device 100, 200 or 400.

Moreover, when replacing the endpiece 104, the new endpieces 104 can be mounted in any orientation or a predetermined orientation about the axis of revolution. The electrical connection between the electrodes 106 and the calculation means 115 is provided by the annular tracks 118 or 202, regardless of the orientation of the endpieces relative to the shaft 110.

Figure 9:
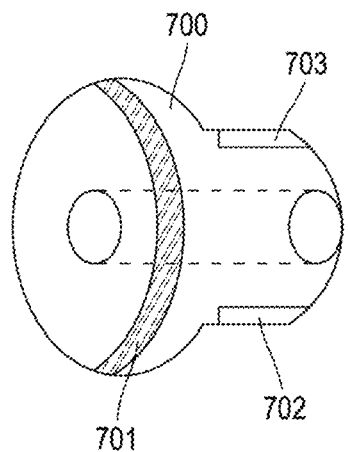
FIG. 9 is a perspective view of an endpiece comprising electrodes according to another embodiment.
Figure 10:
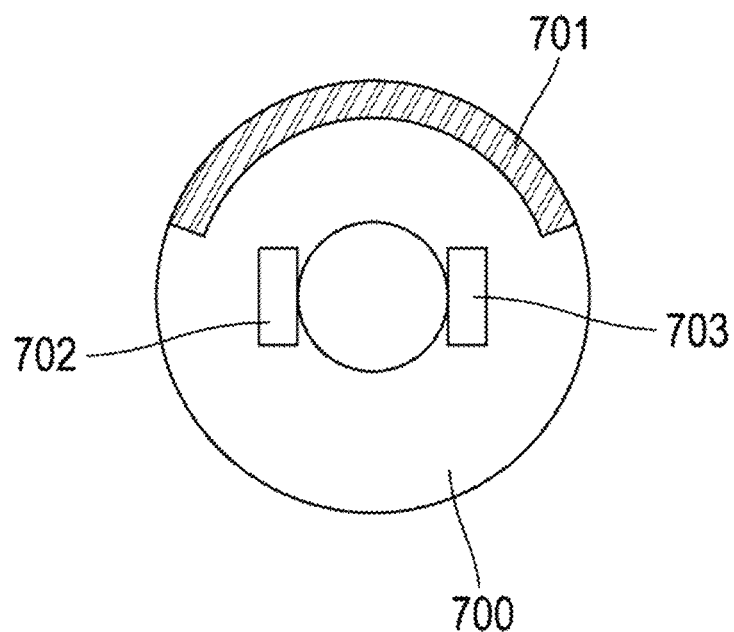
FIG. 10 is a plan view of the endpiece from FIG. 9.

FIGS. 9 and 10 show an embodiment of an endpiece 700 that has three electrodes and can be used in the aforementioned devices 100, 200 and 400. The electrodes 702 and 703, arranged diametrically opposite on either side of the cylindrical part of the endpiece, correspond to a measuring electrode and a reference electrode. The electrode 701, placed farther back in relation to the other two, corresponds to a ground electrode. Its set-back position in relation to the other electrodes allows it to be in contact with the tragus. This is made possible by the convex shape of the endpiece in the part that will be nearest the entrance to the ear canal. Thus, the three electrodes 701, 702 and 703 can be used to perform a measurement, as will be described below with reference to FIG. 11.

It is possible to carry out several parallel recordings in order to increase the accuracy of the measurement. Each additional recording requires an additional electrode (which will be a measuring electrode). To perform two recordings, it is thus possible to add a measuring electrode on the cylindrical part spaced apart in a circumferential direction with respect to the electrodes 702 and 703.

Figure 11:
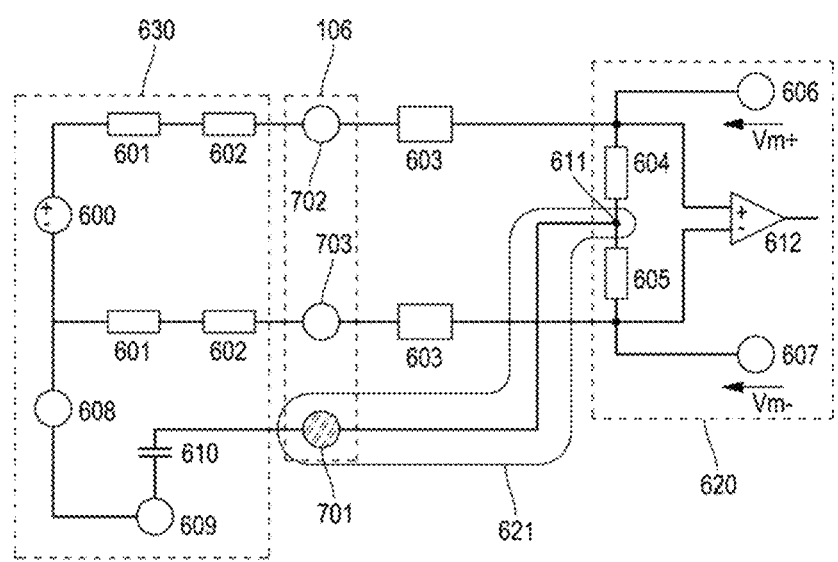
FIG. 11 is an electrical block diagram of an earpiece according to one embodiment, connected to the brain of the mammal.

FIG. 11 shows a block diagram of the functioning of the device provided with the endpiece 700 when it is in use, in contact with the body 630 of a living mammal. The figure shows in particular the electrical circuit making it possible to measure a potential difference between the signal picked up by a measuring electrode and the signal picked up by a reference electrode. The signals originate from the mammalian brain 600. The mammal can be a human, for example.

In FIG. 11, the body 630 is modeled as follows. The mammalian brain 600 is modeled as a voltage generator with internal resistances. The voltage generated is of the order of 100 μV. The internal resistances here are made up of the resistance of the head of the individual 601 and the resistance of the skin of the individual 602. The resistance of the skin of the individual 602 is the most important resistance. This resistance varies between 5 and 100 MΩ. This resistance depends on several more or less controllable parameters. The body 630 also comprises sources of noise. These sources of noise are the electrical generators of the body (facial muscles, eyes, etc.), but also external disturbances which can inject current from time to time into the circuit. The generators of internal noise are modeled by the internal noise generator 608, and the noise sources external to the individual are modeled by the external noise generator 609. The individual's body then acts as an antenna, which can be modeled by a capacitor 610, of variable capacitance depending on the current injected by the external noise generator 609.

In order to determine a physiological or psychological state of the individual, it is necessary to measure a potential difference in the brain 600, that is to say in this instance between the positive and negative terminals of the generator that models the brain. A measuring electrode 702 picks up an electrical signal at the positive terminal, and a reference electrode 703 picks up an electrical signal at the negative terminal. The voltages of the two signals are influenced by the resistances of the individual's head 601 and skin 602, as is shown in the diagram. Each of these signals is conveyed to a measuring device 620 included in the aforementioned processing means 114.

Before arriving at the measuring device 620, each of the two signals is amplified by passing through an impedance adapter 603, which permits 10 to 12 times amplification. The voltage of the current coming from the amplifier is therefore of the order of 10 to 100 µV, while the initial signal has a potential of the order of µV. To measure the voltage of the signal picked up by the measuring electrode 702 and by the reference electrode 703, the measuring device 620 comprises an internal resistance 604, 605, respectively, of a known identical resistance value (in practice close to 1 GΩ). According to one embodiment, the resistance can be a set of resistors connected in series. The measurement is carried out according to the principle of a voltmeter. This resistor is connected to a voltage generator 606 generating a potential Vm+ and a voltage generator 607 generating a potential Vm−. In practice, a value chosen for the potentials is for example Vm+=2.4 V and Vm−=0 V. The signals thus measured are then conveyed to an operational amplifier 612. The measuring device 620 can be produced by means of an ADS 1292 component available from the company Texas Instrument.

This circuit makes it possible to detect the aberrant values during the measurement of the potential difference between the + and − terminals of the generator that models the brain 600. Indeed, the measured potential difference must then fluctuate within 10 or 100 µV around 1.2V A potential difference that deviates significantly from this value is then declared as aberrant. The impedance adapter 603 also makes it possible to limit the aberrant measurements. Indeed, if one of the signals obtained exceeds the window of values between Vm− and Vm+, the impedance adapter 603 does not amplify the signal, and so the measurement is directly detected as being aberrant.

When calculating the potential difference, it is also necessary to remove the noise from the measurement. In the embodiment shown in FIG. 11, the ground electrode 701 is used to suppress the noise from the noise sources external to the individual, which are represented by generator 609. The solution for suppressing the noise is a common-mode rejection circuit 621. For this, the ground electrode 701 is connected to the midpoint 611 between the resistances 604 and 605.

In the modeling adopted, the effect of this connection is to short-circuit the capacitor 610 by injecting into the circuit a current identical to that generated by the external noise generator 609. This current corresponds to the signal picked up by the ground electrode 701 in contact with a very stable zone of the ear canal, in which the electrical signal variations correspond to the variations in external noise. An example of a stable zone of this kind, which is able to capture the purest possible external noise, is the tragus, a cartilage located in the ear at the entrance to the ear canal. In practice, the common-mode rejection circuit 621 is implemented by connecting the ground electrode 701 to a potential corresponding to half the sum of Vm+ and Vm−, so that the zero potential is defined in the same way in the whole circuit. In FIG. 11, it is the midpoint 611 that corresponds to this potential.

Indeed, it is necessary that the zero potential corresponding to the current permitting noise reduction is the same potential around which the measured potential difference fluctuates. With the values given above, the potential difference fluctuates around 1.2V, and so the ground electrode 701 must be connected to this potential of 1.2V.

Figure 12:
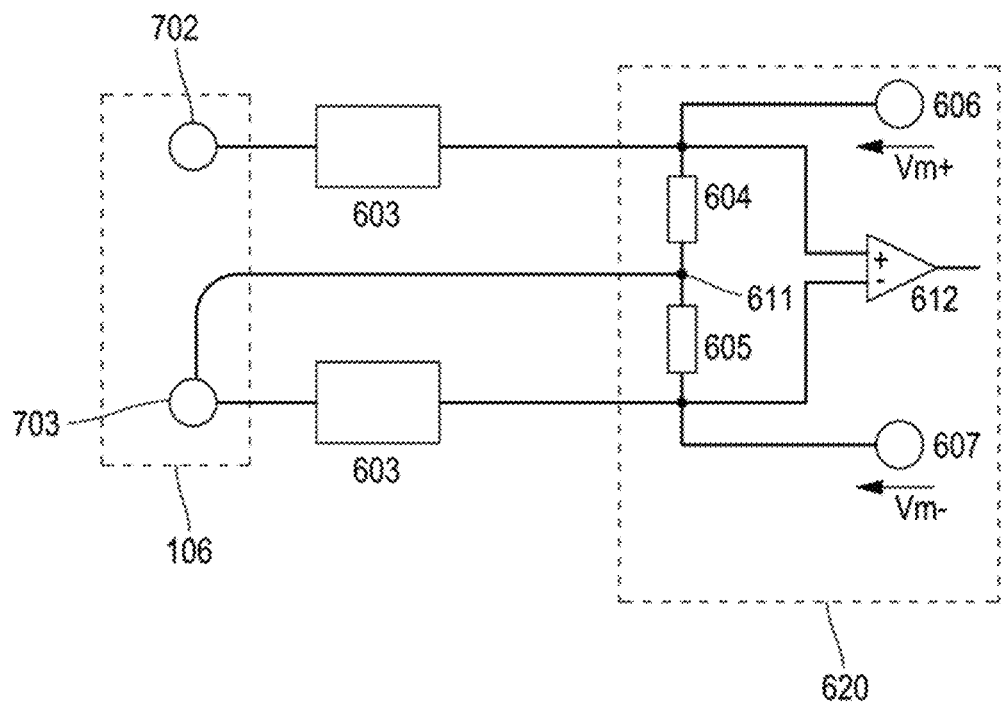
FIG. 12 is an electrical block diagram of an earpiece according to another embodiment, connected to the brain of the mammal.

In the embodiment in FIG. 12, the plurality of electrodes 106 comprises only a measuring electrode 702 and a reference electrode 703. The ground electrode 701 is omitted. The noise from the generator 609 is suppressed by connecting the reference electrode 703 to the midpoint 611 corresponding to half the sum of Vm+ and Vm−. In this embodiment, everything happens as if there were a virtual ground electrode combined with the reference electrode 703.

The uses of such a device 100, 200 or 400 are numerous, especially in medicine, especially for the monitoring of patients with neuronal diseases, including epilepsy, the screening and diagnosis of neuronal diseases, the screening and monitoring of children with attention disorders, but also for the monitoring of certain professionals, in particular the monitoring of air traffic controllers or air pilots, the monitoring of sportsmen and women, or for improving daily life, for example the development of wellness applications.

Although the invention has been described in relation to several particular embodiments, it is quite obvious that it is in no way limited thereto and that it encompasses all the technical equivalents of the means described and their combinations, provided that the latter fall within the context of the invention.

The use of the verb "have", "comprise" or "include" and its conjugated forms does not preclude the presence of elements or steps other than those stated in a claim.

In the claims, any reference sign between parentheses should not be interpreted as limiting the claim.

What is claimed is:

1. A device for determining a physiological or psychological state of a mammal, the device comprising at least one earpiece comprising:
a main body comprising a body of revolution having an axis of revolution;
an endpiece configured to be inserted into a first ear canal, said endpiece having a cylindrical channel intended to receive the body of revolution for detachably mounting the endpiece on the main body, the endpiece being arranged to be movable in rotation about the axis of revolution in order to allow at least one electrode to be oriented toward a zone of a brain of the mammal, and said endpiece comprising a plurality of electrodes arranged on an outer surface of the endpiece, wherein the plurality of electrodes comprises a reference electrode and at least one measuring electrode, each electrode being configured to pick up an electrical signal in the ear canal of the mammal;
first electrical tracks electrically insulated from each other, arranged in the cylindrical channel of the endpiece and connected to the electrodes;
second electrical tracks electrically insulated from each other, arranged in a cylindrical part of the main body and intended to convey the electrical signal, picked up by the electrodes, to a calculation means, wherein each of the first electrical tracks or each of the second electrical tracks has an annular shape having as its axis said axis of revolution and is arranged in electrical contact with one of said first electrical tracks or one of said second electrical tracks, independently of the orientation of the endpiece about said axis of revolution, and said first electrical tracks or second electrical tracks of annular shape being spaced along said axis of revolution;
processing means including two voltage generators which respectively generate a first constant voltage and a second constant voltage; and
calculation means for determining the physiological or psychological state as a function of a potential difference between the electrical signal picked up by the at least one measuring electrode and the electrical signal picked up by the reference electrode, wherein said potential difference fluctuates around a potential corresponding to half a sum of the first and second constant voltages delivered by the two voltage generators.

2. The device as claimed in claim 1, wherein at least one of the electrodes has an outer part extending over a longitudinal part, in a direction of the axis of revolution, of the outer surface of the endpiece.

3. The device as claimed in claim 1, wherein at least one of the electrodes has an inner part extending over a part of the cylindrical channel in order to form the first electrical track.

4. The device as claimed in claim 1, wherein each of the second electrical tracks is annular, and each of the first electrical tracks is configured to come into contact with a respective second annular electrical track.

5. The device as claimed in claim 4, wherein each of the first electrical tracks extends in an arc of a circle on an inner part of the cylindrical channel about the axis of revolution.

6. The device as claimed in claim 1, wherein each of the first electrical tracks is annular, and each of the second electrical tracks forms a contact pad configured to come into contact with a respective first annular electrical track.

7. The device as claimed in claim 1, in which the device comprises two earpieces comprising the at least one measuring electrode and the reference electrode, respectively, configured to be arranged in the first ear canal and a second mammalian ear canal, respectively, and intended to convey respective electrical signals to the calculation means,
said calculation means for determining the physiological or psychological state as a function of the electric signal picked up by the at least one measuring electrode of the earpiece arranged in the first ear canal and the electric signal picked up by the reference electrode of the earpiece arranged in the second mammalian ear canal.

8. The device as claimed in claim 1, further comprising:
a ground electrode, said ground electrode being oriented toward a specific part of the ear canal, said specific part of the ear canal making it possible to pick up a stable signal, said ground electrode being configured to pick up an electrical signal in the ear canal of the mammal; and
wherein the processing means is configured to use the electrical signal picked up by the ground electrode to effect a noise reduction in the signals measured by the reference electrode and the at least one measuring electrode, wherein the ground electrode is connected to the potential corresponding to half a sum of the first and second constant voltages delivered by the two voltage generators.

9. The device as claimed in claim 8, wherein the endpiece is constructed so as to be able to be in contact with the specific part of the ear canal when inserted into the ear canal, and wherein the ground electrode is located on a part of the endpiece in contact with the specific part of the ear canal, in order to pick up the electrical signal on said specific part of the ear canal.

10. The device as claimed in claim 8, wherein the specific part of the ear canal is a mammalian tragus.

11. The device as claimed in claim 8, wherein the noise reduction is achieved by means of a common-mode rejection circuit.

12. The device as claimed in claim 8, wherein the processing means comprise a first resistor connected to a first voltage generator and arranged in such a way as to receive the electrical signal picked up by the reference electrode, and a second resistor connected to a second voltage generator and arranged to receive the electrical signal picked up by the at least one measuring electrode, the second voltage generator delivering a voltage greater than that delivered by the first voltage generator.

13. The device as claimed in claim 1, wherein the plurality of electrodes are spaced apart from each other in a circumferential direction about the axis of revolution.

14. The device as claimed in claim 1, wherein the reference electrode is intended to be oriented toward a mastoid of the mammal upon insertion of the endpiece into the ear canal of the mammal.

15. The device as claimed in claim 1, wherein the endpiece has a marking configured for visually recognizing the reference electrode.

16. The device as claimed in claim 1, comprising a selector configured to receive the signals from the plurality of electrodes, said selector being configured to detect the reference electrode, among the plurality of electrodes, said reference electrode being selected as the electrode emitting the electrical signal having a most stable electrical potential among the signals picked up by the plurality of electrodes.

17. The device as claimed in claim 1, wherein the main body comprises wired or wireless data transmission means configured to communicate with the calculation means.

18. The device as claimed in claim 1, wherein the device comprises a means for filtering the signals, said means for filtering being configured to attenuate parasitic signals detected by one or more of said plurality of electrodes, wherein the means for filtering comprises a band-pass filter having a pass band between 0.3 Hz and 50 Hz.

19. The device as claimed in claim 1, wherein the calculation means is configured to:
determine an electroencephalogram signal of the mammal as a function of the electrical signals measured,
determine an amplitude of at least one brain wave in a predefined frequency range as a function of said electroencephalogram signal, and
determine a psychological state as a function of said amplitude of said at least one brain wave by comparing said amplitude with a predetermined threshold.

20. The device as claimed in claim 1, wherein the physiological or psychological state relates to an electrical activity of an organ of the mammal, selected from the group consisting of a brain, a heart, a nerve, a muscle and an eye.

21. The device as claimed in claim 1, wherein the physiological or psychological state is mammalian fatigue, a mammalian attention level or a mammalian epileptic seizure.

22. The device as claimed in claim 1, wherein the reference electrode is connected to the potential corresponding to half a sum of the first and second constant voltages delivered by the two voltage generators.

* * * * *

UNITED STATES PATENT AND TRADEMARK OFFICE
CERTIFICATE OF CORRECTION

| | | |
|---|---|---|
| PATENT NO. | : 12,263,000 B2 | Page 1 of 1 |
| APPLICATION NO. | : 18/825167 | |
| DATED | : April 1, 2025 | |
| INVENTOR(S) | : Hugo Hung-Cuong Dinh et al. | |

It is certified that error appears in the above-identified patent and that said Letters Patent is hereby corrected as shown below:

On the Title Page

(73) Assignee should read: NAOX TECHNOLOGIES, Palaiseau (FR)

Signed and Sealed this
Twenty-ninth Day of April, 2025

Coke Morgan Stewart
*Acting Director of the United States Patent and Trademark Office*